United States Patent
Kuusisto et al.

(10) Patent No.: US 10,695,313 B2
(45) Date of Patent: Jun. 30, 2020

(54) EDIBLE COMPOSITION SUITABLE FOR LOWERING SERUM CHOLESTEROL

(71) Applicant: RAISIO NUTRITION LTD, Raisio (FI)

(72) Inventors: Päivi Kuusisto, Raisio (FI); Ingmar Wester, Raisio (FI)

(73) Assignee: RAISIO NUTRITION LTD, Raisio (FI)

(*) Notice: Subject to any disclaimer, the term of this patent is extended or adjusted under 35 U.S.C. 154(b) by 0 days.

(21) Appl. No.: 14/901,903

(22) PCT Filed: Jul. 4, 2014

(86) PCT No.: PCT/FI2014/000016
§ 371 (c)(1),
(2) Date: Dec. 29, 2015

(87) PCT Pub. No.: WO2015/001175
PCT Pub. Date: Jan. 8, 2015

(65) Prior Publication Data
US 2016/0143334 A1    May 26, 2016

(30) Foreign Application Priority Data
Jul. 5, 2013  (FI) ..................................... 20130201

(51) Int. Cl.
| A61K 36/00 | (2006.01) |
| A61K 31/23 | (2006.01) |
| A61K 36/185 | (2006.01) |
| A23L 29/30 | (2016.01) |
| A61K 36/73 | (2006.01) |
| A61K 45/06 | (2006.01) |
| A61K 31/575 | (2006.01) |
| A61K 31/232 | (2006.01) |
| A23L 33/11 | (2016.01) |
| A23L 33/15 | (2016.01) |
| A23L 33/135 | (2016.01) |
| A23L 33/115 | (2016.01) |
| A23G 3/48 | (2006.01) |
| A61K 31/047 | (2006.01) |
| A61K 31/7004 | (2006.01) |
| A61K 31/7016 | (2006.01) |
| A61K 31/702 | (2006.01) |
| A61K 36/18 | (2006.01) |

(52) U.S. Cl.
CPC ................ *A61K 31/23* (2013.01); *A23G 3/48* (2013.01); *A23L 29/30* (2016.08); *A23L 29/37* (2016.08); *A23L 33/11* (2016.08); *A23L 33/115* (2016.08); *A23L 33/135* (2016.08); *A23L 33/15* (2016.08); *A61K 31/047* (2013.01); *A61K 31/232* (2013.01); *A61K 31/575* (2013.01); *A61K 31/702* (2013.01); *A61K 31/7004* (2013.01); *A61K 31/7016* (2013.01); *A61K 36/18* (2013.01); *A61K 36/185* (2013.01); *A61K 36/73* (2013.01); *A61K 45/06* (2013.01); *A23V 2002/00* (2013.01)

(58) Field of Classification Search
CPC ...................................................... A61K 36/00
USPC ........................................................ 424/725
See application file for complete search history.

(56) References Cited

U.S. PATENT DOCUMENTS

| 6,174,560 | B1 | 1/2001 | Miettenen et al. |
| 6,491,952 | B1 | 12/2002 | Sjoberg |
| 2003/0044449 | A1 | 3/2003 | Miyanishi et al. |
| 2006/0134294 | A1 | 6/2006 | McKee et al. |
| 2008/0089978 | A1 | 4/2008 | Grigg et al. |
| 2008/0187645 | A1 | 8/2008 | Ekblom et al. |
| 2008/0220051 | A1 | 9/2008 | Horlacher et al. |
| 2008/0261916 | A1 | 10/2008 | Jaszberenyi et al. |
| 2009/0130211 | A1 | 5/2009 | Gamay |
| 2009/0238866 | A1 | 9/2009 | Haug et al. |
| 2010/0166921 | A1 | 7/2010 | Qvyjt |
| 2012/0121621 | A1 | 5/2012 | Jaszberenyi et al. |
| 2012/0308710 | A1 | 12/2012 | Beck et al. |
| 2012/0308711 | A1 | 12/2012 | Schwaier et al. |
| 2013/0266704 | A1 | 10/2013 | Smit-Kingma et al. |

FOREIGN PATENT DOCUMENTS

| CA | 1289074 C | 9/1991 |
| CN | 102415465 A | 4/2012 |
| DE | 102005039835 A1 | 3/2007 |
| EP | 1011343 A1 | 6/2000 |
| EP | 1074185 A1 | 2/2001 |
| EP | 1762146 A1 | 3/2007 |
| EP | 1827137 A1 | 9/2007 |
| EP | 2255669 A1 | 12/2010 |
| EP | 2286671 A1 | 2/2011 |

(Continued)

OTHER PUBLICATIONS

Arjen Bot et al: 11 Structuring in 1-59-sitosterol-oryzanol-based emulsion gels during various states of a temperature cycle. Food Hydrocolloi DS. Elsevier BV. NL. vol. 25. No. 4. Jul. 28, 2010 (Jul. 28, 2010). pp. 639-646.

(Continued)

*Primary Examiner* — Michael V Meller
(74) *Attorney, Agent, or Firm* — Harness, Dickey & Pierce, P.L.C.

(57) ABSTRACT

The present invention relates to an edible composition comprising plant sterol ester and/or plant stanol ester and triglyceride fat usable for lowering serum LDL cholesterol. The composition further comprises oligosaccharides and sugars. The composition can preferably be used in dietary supplements, fillings and toppings.

18 Claims, No Drawings

(56) References Cited

FOREIGN PATENT DOCUMENTS

| | | |
|---|---|---|
| EP | 2446745 A1 | 5/2012 |
| FI | 125947 B | 4/2016 |
| GB | 2430344 A | 3/2007 |
| WO | 1997/042830 A1 | 11/1997 |
| WO | 2000/041491 A2 | 7/2000 |
| WO | 200234057 A2 | 5/2002 |
| WO | 2002/065859 A1 | 8/2002 |
| WO | 2005096831 A1 | 10/2005 |
| WO | WO-2006/037847 A1 | 4/2006 |
| WO | WO-2006/063219 A2 | 6/2006 |
| WO | WO-2006/134409 A2 | 12/2006 |
| WO | WO-2007/057511 A1 | 5/2007 |
| WO | 2009/068651 A1 | 6/2009 |
| WO | 2011/095305 A1 | 8/2011 |
| WO | 2012/046066 A1 | 4/2012 |
| WO | WO-2012/084416 A1 | 6/2012 |

OTHER PUBLICATIONS

Third Party Observation dated Mar. 2, 2017 for EP2014070243 (a corresponding application to FI priority appln 20130201).
Finnish Patent and Registration Office Search Report dated Mar. 11, 2014.
International Search Report and Written Opinion of the ISA, ISA/EP, Rijswij, NL, dated Oct. 22, 2014.

EDIBLE COMPOSITION SUITABLE FOR LOWERING SERUM CHOLESTEROL

CROSS-REFERENCE TO RELATED APPLICATIONS

This application is a 371 U.S. National Stage of International Application No. PCT/FI2014/000016, filed in English on Jul. 4, 2014. This application claims the benefit of and priority to Finnish Patent Application No. 20130201, filed Jul. 5, 2013. The entire disclosures of the above applications are incorporated herein by reference.

FIELD OF THE INVENTION

The present invention relates to an edible composition having serum LDL cholesterol lowering effect, and especially to a dietary supplement containing plant sterol ester and/or plant stanol ester.

BACKGROUND OF THE INVENTION

Cardiovascular disease is counted among the most common diseases in Western countries and its occurrence is further increasing. The most important individual risk factor is elevated serum LDL cholesterol level, and therefore, lowering of the cholesterol level is the most effective single measure regarding both prevention and effective treatment of cardiovascular disease.

The most important drugs for reduction of cholesterol levels are the statins, which primarily function by inhibiting the synthesis of cholesterol in the liver. The most common side effects of the statins are gastrointestinal, other less common side effects include headache, dizziness, rash, and sleep disturbances. In addition, statins may cause both liver damage and muscle disorders.

As an alternative, or in addition to medical treatment and the use of conventional drugs, attention has during the last decades been focused on reducing the risk for cardiovascular diseases by means of changing life style, in particular by increasing physical exercise, and adopting a low-fat or low-cholesterol diet. Another nutritional way to affect the cholesterol levels is to use cholesterol lowering agents in functional foods that can be a part of a conventional diet. This alternative has been greatly welcomed by consumers.

Food products enriched with components having cholesterol lowering effect have been commercially available for more than 15 years. Such food products usually contain plant sterols and/or plant stanols and especially their esters as active ingredient. Plant sterols have since the 1950's been known to effectively reduce serum cholesterol levels. U.S. Pat. No. 6,174,560 describes plant stanol fatty acid esters, a method for their preparation, and the cholesterol lowering effects thereof. An intake of 2 g per day of plant stanols is reported to lower serum LDL cholesterol levels in man up to 14%. Benecol® is a well-known trademark that nowadays is used in a large group of food products.

However, many consumers prefer to have their daily dose of plant sterol ester and/or plant stanol ester available in an easier form that can be carried along wherever they go, e.g. as a dietary supplement. This more corresponds to taking a drug like statin, and persons being used to take statins could easily at the same time have a plant sterol ester and/or plant stanol ester dose to further improve the lowering of their serum LDL cholesterol.

Dietary supplements based on plant sterol ester and/or plant stanol ester are currently marketed mainly as so-called soft gelatine capsules. However, one problem with this type of product is that the size of the soft gelatine capsule is big, causing problems with the swallowing of it. Such soft gelatine capsules typically deliver about 1 g plant sterol ester and/or plant stanol ester contained in each soft gelatine capsules. This means that the consumer has to swallow several big soft gelatine capsules per day to obtain the daily recommended amount of plant sterol ester and/or plant stanol ester. Many consumers have difficulties in swallowing such big capsules. Furthermore, the swallowing of such capsules involves simultaneous drinking of water or some other liquid and the capsules are therefore not so convenient to use.

Also chewable plant sterol ester and/or plant stanol ester dietary supplements have been described. However, the plant sterol ester and/or plant stanol ester concentration of the prior known chewable dietary supplement products is low, thus consumers need to take several servings of them to get the daily dose of plant sterol ester and/or plant stanol ester. Prior known dietary supplements also contain components, such as adsorbents, emulsifiers or other E-numbered additives, that are not desired by consumers in food products. Further, some of them contain a lot of sugar, which is not desired either. There is a need for a plant sterol ester and/or plant stanol ester composition that can be used as a chewable dietary supplement, and has a high plant sterol ester and/or plant stanol ester content, a low monosaccharide and disaccharide content, and good organoleptic properties, especially mouthfeel and texture. Further, dietary supplements with high triglyceride fat content would be advantageous, as the fat simultaneously ingested with plant sterol ester and/or plant stanol ester is thought to ensure effective cholesterol lowering. It would also be advantageous to have compositions with versatile usage. Also compositions that can be stored at room temperatures, and do not require refrigeration would be advantageous. Also a simple manufacturing method is beneficial. The current invention satisfies at least one, and preferably all of these needs.

BRIEF DESCRIPTION OF THE INVENTION

The present invention is directed to an edible composition, which comprises
  total fat in an amount of at least 50% by weight, wherein the total fat comprises a mixture of a) plant sterol ester and/or plant stanol ester and b) triglyceride fat, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat,
  at least one monosaccharide, disaccharide or sugar alcohol in such an amount that the total amount of monosaccharides, disaccharides and sugar alcohols is at most 18% by weight,
  at least one oligosaccharide in such an amount that the ratio of the total amount of oligosaccharides to the total amount of monosaccharides, disaccharides and sugar alcohols is from 1:0.2 to 1:0.9, and
  moisture in an amount of at most 8% by weight.

The invention is also directed to a method for preparing the composition, wherein it comprises following steps:
  melting the plant sterol ester and/or plant stanol ester, preferably at a temperature of at least 40° C., more preferably at 40-80° C., mixing the melted plant sterol ester and/or plant stanol ester with the triglyceride fat, which has preferably been melted, preferably at a temperature of at least 40° C., more preferably at 40-80° C., mixing the obtained fat mixture, which has a temperature of at least 40° C., more preferably 40-80° C. to avoid its crystallization, with the other ingredients, optionally forming the desired shapes, and optionally packaging the composition, the method preferably excluding any step of adding water and/or cooking the mixture of ingredients to substantially reduce the moisture content of the mixture of ingredients during the preparation of the composition.

The invention is further directed to the use of the edible composition for preparing a dietary supplement, or a biscuit or wafer with the composition as filling or topping. The invention is also directed to the edible composition for use as a medicament and/or for lowering serum LDL level.

DETAILED DESCRIPTION OF THE INVENTION

It is thus an object of the present invention to provide an edible composition having a high total fat content and a high plant sterol ester and/or plant stanol ester content, a low content of total monosaccharides, disaccharides and sugar alcohols, and good organoleptic properties, especially mouthfeel and texture. The composition has a serum LDL cholesterol lowering effect.

It was surprisingly found that an edible composition having a high plant sterol ester and/or plant stanol ester content, a high total fat content and a low total monosaccharide, disaccharide and sugar alcohol content with good organoleptic properties could be produced by combining oligosaccharide with monosaccharide, disaccharide and/or sugar alcohol in certain ratios. Less monosaccharides, disaccharides and/or sugar alcohols could be used than in prior known products.

Surprisingly it was also noticed that when the composition has a high weight ratio of plant sterol ester and/or plant stanol ester to the oligosaccharides, and/or a high weight ratio of plant sterol ester and/or plant stanol ester to the total amount of monosaccharides, disaccharides and/or sugar alcohols, it has good organoleptic properties. Also when the weight ratio of the total fat to the oligosaccharides is high, the composition has good organoleptic properties.

One of the advantages of the composition is that, in addition to a high amount of plant sterol ester and/or plant stanol ester, it has also a high triglyceride fat content. Triglyceride fat facilitates the cholesterol lowering effect of plant sterol ester and/or plant stanol ester.

The composition of the present invention has also versatile usage: it can be used as a dietary supplement or as a filling or topping, such as a filling or topping for biscuits or wafers. The composition can be ingested without simultaneously drinking of water or some other liquid, so the composition is convenient to use. The composition has good organoleptic properties. It is chewable and non-powdery. The mouthfeel is not gritty, not powdery, not chalky or sticky. The mouthfeel is not fatty or oily either, although the composition contains a lot of triglyceride fat as well as a lot of plant sterol ester and/or plant stanol ester. The composition melts in the mouth, and does not leave "gum like" pieces. It can be chewed, is easily processed and cut, but the texture is not too soft. The composition can be stored at room temperature, so it does not require refrigerated storage.

The composition does not melt or disintegrate at room temperature. It is not adhesive e.g. to package material or to hands.

Thus, the present invention is directed to a serum LDL cholesterol lowering edible composition, which comprises total fat in an amount of at least 50% by weight, wherein the total fat comprises a mixture of a) plant sterol ester and/or plant stanol ester and b) triglyceride fat, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat, at least one monosaccharide, disaccharide or sugar alcohol in such an amount that the total amount of monosaccharides, disaccharides and sugar alcohols is at most 18% by weight, at least one oligosaccharide in such an amount that the ratio of the total amount of oligosaccharides to the total amount of monosaccharides, disaccharides and sugar alcohols is from 1:0.2 to 1:0.9, and moisture in an amount of at most 8% by weight.

By "edible composition" is here meant a composition containing only components that are permitted in food products. By "chewable" is meant a composition that is easy to chew at mouth temperature. At room temperature (e.g. 25° C.) these compositions are usually solid, but can easily be cut e.g. with a knife. The composition being "solid" means that the composition retains its three dimensional shape at room temperature. Practically, the composition is solid enough for one to pick it with one's fingers from the package. When the temperature is raised, the composition is softened. Preferably the composition melts in the mouth. By "non-powdery" is meant that the composition is not in a form of powder and does not give a powdery mouthfeel. By "uncooked" is meant that the mixture of ingredients of the composition has not been cooked during the preparation of the composition. Cooking here means heat treatment to reduce the water content of the mixture of ingredients. Therefore, uncooked means that the water content of the composition has not been substantially reduced by heating during preparation of the composition, i.e. the water content contained in the mixture of all the ingredients used is substantially the same as the water content of the composition according to the invention (typically at most 10% reduction of the water content, more typically at most 5% reduction). By "ungelled" is meant that the mixture of ingredients has not gelled during the preparation of the composition. Because water (also meaning any component with high water content) is not added, and the main ingredients (plant sterol ester and/or plant stanol ester; triglyceride fat; monosaccharides, disaccharides and/or sugar alcohols; and oligosaccharides) have a very low water content, and further the preparation method does not include any cooking step, gelling of the ingredients does not happen. The composition according to the invention is chewable and non-powdery. It is further ungelled and/or uncooked.

Preferably the edible composition is a dietary supplement. By "dietary supplement" is meant edible products that are not presented or marketed as conventional food products, but are used to supplement the diet with plant sterol ester and/or plant stanol ester, and to influence the cholesterol metabolism. In this disclosure, the term "dietary supplement" also covers edible products that fulfil the aforementioned definition, but can be presented or marketed in some countries for similar purposes such as "a medical food" or "a medical device". The supplements are taken in small doses and they do not substitute for meals or for a daily diet. Preferably the supplement is in the form of a chew.

The edible composition may also be a filling or topping. By "filling or topping" is meant fillings and toppings for bakery products, preferably fillings and toppings for biscuits and wafers. Especially fillings that are used in products having the filling placed between two pieces of biscuits or wafers are preferred.

The edible composition according to the invention comprises total fat in an amount of at least 50% by weight. By "total fat" is meant all lipid compounds in the composition. "Total fat" comprises the mixture of plant sterol ester and/or plant stanol ester and triglyceride fat. "Total fat" may contain also other lipid compounds, such as free (unesterified) sterols and/or stanols in small amounts. Preferably the amount of free sterols and/or stanols is at most 15%, more preferably at most 10% and most preferably at most 5% of the total fat. Preferably "total fat" is the mixture of plant sterol ester and/or plant stanol ester and triglyceride fat. The total fat content of the composition can be analysed by methods commonly used in the art. Typically the methods include extracting the fat soluble compounds with organic solvents, such as for example hexane, heptane, chloroform, methanol, diethyl ether, petroleum ether or mixtures thereof, evaporating the solvent and weighing of the amount of the "total fat". Preferably the extraction is performed with petroleum ether.

The amount of total fat is at least 50% by weight of the composition. More specifically the amount of total fat is 50-80% by weight, preferably 55-80%, more preferably 60-75%, most preferably 60-70% by weight of the composition.

The edible composition according to the invention contains plant sterol ester and/or plant stanol ester. As used here, the term "plant sterol ester and/or plant stanol ester" refers to plant sterols and/or plant stanols in esterified form.

In this specification the term "plant sterols" includes 4-desmethyl sterols and 4-monomethyl sterols and the term "plant stanols" includes 4-desmethyl stanols and 4-monomethyl stanols. Typical 4-desmethyl sterols are sitosterol, campesterol, stigmasterol, brassicasterol, 22-dehydro-brassicasterol and δ5-avenasterol. Typical stanols are sitostanol, campestanol and their 24-epimers. The term "plant sterols and/or plant stanols" includes all possible mixtures of named sterols and/or stanols as well as any individual sterol and/or stanol.

In this invention the term "plant sterol ester and/or plant stanol ester" refers to plant sterols and/or plant stanols that are esterified with a carboxylic acid or with a blend of carboxylic acids and are called "plant sterol ester and/or plant stanol ester". Examples of suitable carboxylic acids are fatty acids (2-24 carbon atoms, saturated, monounsaturated or polyunsaturated, including also special fatty acids, such as conjugated fatty acids e.g. CLA, and EPA and DHA). Preferably the plant sterols and/or plant stanols are esterified with vegetable oil based fatty acids. Most preferred are plant stanol fatty acid esters. Therefore, "the plant sterol ester and/or plant stanol ester" comprises preferably plant stanol ester in an amount of at least 10%, more preferably at least 50%, still more preferably at least 70% and most preferably at least 90% by weight. At 25° C. the plant sterol ester and/or plant stanol ester preferably has a solid fat content (SFC) of at least 20%, more preferably at least 30%, still more preferably at least 40%, even more preferably at least 45% and most preferably at least 50%. The solid fat content can be measured e.g. by NMR.

Plant stanol fatty acid ester and the effects thereof, as well as a suitable method for its preparation, are disclosed in U.S. Pat. No. 6,174,560. Obviously also plant sterol esters can efficiently be produced by the production method disclosed in U.S. Pat. No. 6,174,560. Alternatively fatty acid esters of plant sterols and/or plant stanols can be produced by any suitable method disclosed in the art. Commercially available plant sterol ester and/or plant stanol ester ingredients e.g. from BASF or Raisio Nutrition Ltd can be used.

The effects of plant sterols and/or plant stanols has been found additive both to the effect of statins and to the effect of healthy diets, such as low-saturated-fat and low-cholesterol diets. Also the composition of the present invention can be used both as such and in addition to drugs and/or natural components having cholesterol lowering effect.

According to the invention the amount of plant sterol ester and/or plant stanol ester is at least 40% by weight of the total fat, and at least 30% by weight of the composition. More specifically, the amount of the plant sterol ester and/or plant stanol ester is at least 34%, preferably at least 37%, more preferably at least 40%, most preferably at least 42% by weight of the composition. Preferably the amount of the plant sterol ester and/or plant stanol ester is at most 64%, more preferably at most 60%, still more preferably at most 58% and most preferably at most 56% by weight of the composition. When calculated of the total fat, the amount of plant sterol ester and/or plant stanol ester preferably is 40-80%, more preferably 42-75%, still more preferably 45-73%, even more preferably 50-70%, further more preferably 55-70% and most preferably 60-70% by weight of the total fat.

By "triglyceride fat" is meant edible fats and oils that consist mainly (at least 90, preferably at least 95 and most preferably at least 98% by weight) of triacylglycerols. Triglyceride fat can also be a mixture of different edible fats and/or oils. The triglyceride fats can be naturally occurring or modified, for example hydrogenated, fractionated, transesterified or contain structured triacylglycerols. Examples of triglyceride fats are vegetable oils and fats, as well as triglyceride fat of dairy origin. Preferably the triglyceride fat comprises vegetable fats, more preferably cocoa butter, cocoa butter substitute, cocoa butter replacer and/or cocoa butter equivalent. Most preferably the triglyceride fat is cocoa butter, cocoa butter substitute and/or cocoa butter equivalent. Preferably the triglyceride fat has a solid fat content (SFC) of at least 30%, more preferably at least 35%, still more preferably at least 40%, even more preferably at least 45% and most preferably at least 50% at 25° C. The solid fat content can be measured e.g. by NMR.

The amount of triglyceride fat is at least 10% by weight of the composition according to the invention. More specifically, the amount of triglyceride fat is at least 15%, preferably at least 17%, more preferably more than 20%, still more preferably at least 22%, even more preferably at least 24%, and most preferably at least 25% by weight of the composition. Preferably the amount of triglyceride fat is at most 35%, more preferably at most 33%, and most preferably at most 30% by weight of the composition.

The total fat in the composition preferably has a solid fat content (SFC) of at least 40%, more preferably at least 45%, and most preferably at least 50% at 25° C. The solid fat content can be measured e.g. by NMR.

The mixture of plant sterol ester and/or plant stanol ester and triglyceride fat preferably melts at a temperature range 30-45° C. and more preferably at 33-43° C. Most preferably the mixture melts at mouth temperature.

By "monosacharide" is meant a carbohydrate consisting of one sugar molecule. Examples of monosaccharides include e.g. glucose (dextrose), fructose, galactose and xylose. By "disaccharide" is meant a carbohydrate consisting of two sugar molecules. Examples of disaccharides are e.g. sucrose, lactose and maltose. By "sugar alcohol" is meant a hydrogenated form of carbohydrate, whose carbonyl group has been reduced to a primary or secondary hydroxyl group. Examples of "sugar alcohols" include e.g. sorbitol, erythritol, xylitol, mannitol, lactitol, isomalt and maltitol.

The composition according to the invention comprises at least one monosaccharide, disaccharide and/or sugar alcohol. The total amount of monosaccharides, disaccharides and sugar alcohols is at most 18% by weight of the composition. Preferably the total amount of monosaccharides, disaccharides and sugar alcohols is at most 16%, more preferably at most 15% by weight of the composition. More specifically, the total amount of monosaccharides, disaccharides and sugar alcohols is 2-18%, preferably 3-16%, and most preferably 5-15% by weight of the composition.

By "oligosaccharide" is meant a carbohydrate that is composed of several monosaccharide residues (the degree of polymerization, DP, is from three to twenty) joined through glycosidic linkage. Examples of oligosaccharides include maltodextrins, dextrins, fructo-oligosaccharides and galacto-oligosaccharides. Preferably the oligosaccharide comprise maltodextrin. Most preferably the oligosaccharide is maltodextrin. Chemically maltodextrin is an oligosaccharide containing from three to less than 20 glucose residues. Commercially available maltodextrin products may be used as a source of oligosaccharides, although they typically contain also a small amount of glucose and maltose. Commercial maltodextrin products containing at least 90%, preferably at least 92% and more preferably at least 94 wt-% oligosaccharides are suitable for use in the invention. A commercial maltodextrin product having a DE (dextrose equivalent) from 10 to 18, most preferably from 15 to 18 is a preferred source of oligosaccharides.

The amount of oligosaccharides is at least 10%, preferably at least 14%, more preferably at least 18%, most preferably at least 20% by weight of the composition. The amount of oligosaccharides is preferably at most 30%, more preferably at most 28%, and most preferably at most 25% by weight of the composition.

It has been realised that when the composition has a high weight ratio of plant sterol ester and/or plant stanol ester to the oligosaccharides, it has good organoleptic properties. The composition gives no oily or fatty mouthfeel. Preferably the weight ratio of the plant sterol ester and/or plant stanol ester to the oligosaccharide is at least 1.0, more preferably at least 1.3, still more preferably at least 1.5, even more preferably at least 1.7 and most preferably at least 2.0. Preferably the weight ratio of the plant sterol ester and/or plant stanol ester to the oligosaccharide is at most 6.4, more preferably at most 6.0, still more preferably at most 5.0, even more preferably at most 4.0 and most preferably at most 3.5.

Also the weight ratio of the total fat to the oligosaccharides is high. Preferably the weight ratio of the total fat to the oligosaccharide is at least 1.4, more preferably at least 2.0, still more preferably at least 2.5, even more preferably at least 2.7 and most preferably at least 3.0. Despite this high weight ratio, the composition has no oily or fatty mouthfeel. Preferably the weight ratio of the total fat to the oligosaccharide is at most 8.0, more preferably at most 7.0 still more preferably at most 6.0, even more preferably at most 5.5 and most preferably at most 5.0.

Also when the weight ratio of plant sterol ester and/or plant stanol ester to the total amount of monosaccharides, disaccharides and/or sugar alcohols is high, the organoleptic properties of the composition are good. Preferably the weight ratio of the plant sterol ester and/or plant stanol ester to the total amount of monosaccharides, disaccharides and sugar alcohols is at least 1.7, more preferably at least 2.0, still more preferably at least 2.5, even more preferably at least 3.0 and most preferably at least 3.5.

In the composition according to the invention the ratio of total oligosaccharides to the total amount of monosaccharides, disaccharides and sugar alcohols is from 1:0.2 to 1:0.9. More specifically, the ratio of oligosaccharides to the total amount of monosaccharides, disaccharides and sugar alcohols is preferably from 1:0.2 to 1:0.8, and most preferably from 1:0.2 to 1:0.7.

The protein content of the composition is low, preferably less than 10% by weight of the composition. More preferably the protein content is less than 5%, still more preferably less than 3% and even further preferably less than 1% by weight of the composition. The most preferred composition does not contain protein, i.e. the composition is substantially protein-free.

The starch content of the composition is low, preferably less than 5% by weight of the composition. More preferably the starch content is less than 4%, still more preferably less than 3% and even further preferably less than 2% by weight of the composition. The most preferred composition does not contain starch, i.e. the composition is substantially starch-free.

The amount of hydrocolloids in the composition is low, preferably less than 2% by weight of the composition. Examples of the hydrocolloids include xanthan, guar, alginate, gellan, gum Arabic, pectin, carrageenan, locus bean gum. More preferably the hydrocolloid content is less than 1.5%, still more preferably less than 1.0% and even further preferably less than 0.5% by weight of the composition. The most preferred composition does not contain hydrocolloids, i.e. the composition is substantially hydrocolloid-free.

Preferably the composition of the invention does not contain any emulsifier, i.e. the composition is substantially emulsifier-free. By emulsifier is meant small molecule compounds that promote the formation of an emulsion. Examples of such emulsifiers are mono- and diglycerides and their derivatives, sorbitan esters, polysorbates, stearoyl lactylates, sucrose esters, lecithin and its derivatives.

The composition may contain other ingredients, such as flavorings, preparations from fruits and berries, such as berry powders and fruit powders, cocoa powder, artificial sweeteners, colorants and/or preservatives. The composition may also contain ingredients with beneficial health effects, such as vitamins (e.g. C, D, E and K vitamins), antioxidants, polyphenols and/or probiotics.

Preferably the composition according to the invention consists of total fat in an amount of at least 50% by weight, wherein the total fat comprises a mixture of a) plant sterol ester and/or plant stanol ester and b) triglyceride fat, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat, at least one monosaccharide, disaccharide or sugar alcohol in such an amount that the total amount of monosaccharides, disaccharides and sugar alcohols is at most 18% by weight, at least one oligosaccharide in such an amount that the ratio of the total amount of oligosaccharides to the total amount of monosaccharides, disaccharides and sugar alcohols is from 1:0.2 to 1:0.9, moisture in an amount of at most 8% by weight, and one or more other ingredients selected from the group consisting of flavorings; preparations from fruits and berries, such as berry powders and fruit powders; cocoa powder; artificial sweeteners; colorants; preservatives; and ingredients with beneficial health effects, such as vitamins, antioxidants, polyphenols and/or probiotics.

More preferably the composition according to the invention consists of total fat in an amount of at least 50% by weight, wherein the total fat comprises a mixture of a) plant sterol ester and/or plant stanol ester and b) triglyceride fat, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat, at least one monosaccharide, disaccharide or sugar alcohol in such an amount that the total amount of monosaccharides, disaccharides and sugar alcohols is at most 18% by weight, at least one oligosaccharide in such an amount that the ratio of the total amount of oligosaccharides to the total amount of monosaccharides, disaccharides and sugar alcohols is from 1:0.2 to 1:0.9, moisture in an amount of at most 8% by weight, and one or more other ingredients selected from the group consisting of flavorings; preparations from fruits and berries, such as berry powders and fruit powders and/or cocoa powder.

An advantage of the composition of the invention is the simple preparation method. No water is added in the method. There is also no need for cooking the composition. The method does not include any cooking step, which means that water is not removed in any substantial amount during the preparation. The preparation of the composition does preferably not require usage of emulsifiers or other E-numbered food additives Many consumers want to avoid products having a lot of additives.

The composition of the present invention may be produced by methods known in the art. The composition is prepared without adding water. As used here "not adding water" also excludes adding ingredients with high content of water that would rise the water content of the composition above 8% (typically ingredients having more than 50%, more typically more than 20% by weight water are not used). Therefore, the water content of the mixture of all ingredients is at most 8% by weight. The preparation is a simple process and does not include any cooking phase. The plant sterol ester and/or plant stanol ester is melted, preferably at a temperature of at least 40° C., and mixed with the triglyceride fat, which may also have been melted, preferably at a temperature of at least 40° C. The temperature of this fat mixture is kept at least at 40° C., preferably at 40-80° C., to avoid any crystallization of the fat mixture, and the other ingredients are then mixed with the mixture of a) plant sterol ester and/or plant stanol ester and b) triglyceride fat. Optionally, some of the components, for example oligosaccharide and melted plant sterol and/or plant stanol ester, may be pre-mixed and e.g. spray dried to a powder, and the other ingredients added into this powder. Once the composition is ready, it is optionally formed into desired shapes, such as into supplements or biscuit fillings, and finally optionally packed. Water is not added in the preparation process of the composition, so the water content of the composition is low. The composition contains at most 8%, more preferably at most 6%, even more preferably at most 4% and most preferably at most 3% water. The preparation method excludes any step of adding water and/or cooking the mixture of ingredients to substantially reduce its moisture content. This means that the water content of the mixture of all ingredients is reduced less than 10%, preferably less than 5% and most preferably the original water content of the mixture of the ingredients is remained at the same level through the preparation method. Because water is not added and the preparation method does not include any cooking step, gelling of the ingredients does not happen.

Thus, the present invention is also directed to a method for preparing the edible composition, wherein the method comprises following steps:

melting the plant sterol ester and/or plant stanol ester, preferably at a temperature of at least 40° C., more preferably at 40-80° C., mixing the melted plant sterol ester and/or plant stanol ester with the triglyceride fat, which has preferably been melted, preferably at a temperature of at least 40° C., more preferably at 40-80° C., mixing the obtained fat mixture, which has a temperature of at least 40° C., more preferably 40-80° C. to avoid its crystallization, with the other ingredients, optionally forming the desired shapes, and optionally packaging the composition, the method preferably excluding any step of adding water and/or cooking the mixture of ingredients to substantially reduce the moisture content of the mixture of ingredients during the preparation of the composition.

Also a method for preparing a dietary supplement is disclosed. The method contains at least the following steps:

melting the plant sterol ester and/or plant stanol ester, preferably at a temperature of at least 40° C., more preferably at 40-80° C., mixing the melted plant sterol ester and/or plant stanol ester with the triglyceride fat, which has preferably been melted, preferably at a temperature of at least 40° C., more preferably at 40-80° C., mixing the obtained fat mixture, which has a temperature of at least 40° C., more preferably 40-80° C. to avoid its crystallization, with the other ingredients, forming the desired shapes, and packaging the composition, the method preferably excluding any step of adding water and/or cooking the mixture of ingredients to substantially reduce the moisture content of the mixture of ingredients during the preparation of the composition.

The composition is suitable to be used as a chewable dietary supplement as such. Preferably the composition is formed into a desired shape, e.g. by dosing it into moulds. The composition is then packed. Preferably each piece of the composition is individually packed. Each piece of the composition may be for example individually wrapped or packed in a blister pack. However, the composition may also be coated with edible coating to form a dietary supplement product. Preferably the coating is a chewable coating. Preferably the composition is used as such, but it may also be used as a filling or topping for bakery products such as biscuits or wafers.

Because the composition has a high plant sterol ester and/or plant stanol ester content, the daily dose of plant sterol ester and/or plant stanol ester can be incorporated in a small amount of the composition. Thus, if the composition is used as a dietary supplement, one serving of the supplement can provide the daily dose of plant sterol ester and/or plant stanol ester. If the composition is used as a filling or topping, for example as a biscuit or wafer filling or topping, one serving of the biscuit or wafer can provide the daily dose of plant sterol ester and/or plant stanol ester.

The daily dose of plant sterol ester and/or plant stanol ester is at least 2.0 g, preferably at least 2.5 g, more preferably at least 3.0 g and most preferably at least 3.4 g plant sterol ester and/or plant stanol ester. The daily dose of plant sterol ester and/or plant stanol ester is provided by 4-25 g of the composition. Preferably the daily dose is provided by 5-20 g, more preferably by 5-15 g, most preferably by 6-10 g of the composition. Preferably the daily dose of plant sterol ester and/or plant stanol ester is provided by one serving of the composition, i.e. the size of a serving being preferably 4-25 g, more preferably 5-20 g, still more preferably 5-15 g and most preferably 6-10 g. A serving consists of one or more pieces of the composition, and preferably a serving is one piece of the composition. Preferably the daily dose of plant sterol ester and/or plant stanol ester is provided by one serving of the composition being in one piece, e.g. in one dietary supplement or in one biscuit. Most preferred is a dietary supplement providing at least 3.4 g of plant sterol ester and/or plant stanol ester in one serving in 6-10 g of composition.

One preferred embodiment of the present invention is a serum LDL cholesterol lowering edible composition, which comprises
  total fat in an amount of 60-70% by weight, wherein the total fat comprises a mixture of a) plant sterol ester and/or plant stanol ester and b) triglyceride fat, the amount of plant sterol ester and/or plant stanol ester being at least 42% by weight of the composition and the amount of triglyceride fat being at least 25% by weight of the composition, provided that the amount of plant sterol ester and/or plant stanol ester is 50-70% by weight of the total fat,
  at least one monosaccharide, disaccharide or sugar alcohol in such an amount that the total amount of monosaccharides, disaccharides and sugar alcohols is 5-15% by weight,
  at least one oligosaccharide in such an amount that the ratio of the total amount of oligosaccharides to the total amount of monosaccharides, disaccharides and sugar alcohols is from 1:0.2 to 1:0.9, and
  moisture in an amount of at most 8% by weight.

In this embodiment the plant sterol ester and/or plant stanol ester comprises preferably plant stanol ester in an amount of at least 10%, more preferably at least 50%, still more preferably at least 70% and most preferably at least 90% by weight. The plant sterol ester and/or plant stanol ester has preferably a solid fat content (SFC) of at least 20%, more preferably at least 30%, still more preferably at least 40%, even more preferably at least 45% and most preferably at least 50% at 25° C.

In this embodiment, the amount of triglyceride fat is preferably at most 35%, more preferably at most 33% and most preferably at most 30% by weight of the composition. The triglyceride fat has preferably a solid fat content (SFC) of at least 30%, more preferably at least 35%, still more preferably at least 40%, even more preferably at least 45% and most preferably at least 50% at 25° C.

Further in this embodiment, the total fat in the composition preferably has a solid fat content (SFC) of at least 40%, more preferably at least 45%, and most preferably at least 50% at 25° C.

In this embodiment, the weight ratio of the plant sterol ester and/or plant stanol ester to the oligosaccharide is preferably at least 1.0, more preferably at least 1.3, still more preferably at least 1.5, even more preferably at least 1.7 and most preferably at least 2.0. The weight ratio of the plant sterol ester and/or plant stanol ester to the oligosaccharide is preferably at most 6.4, more preferably at most 6.0, still more preferably at most 5.0, even more preferably at most 4.0 and most preferably at most 3.5. The weight ratio of the plant sterol ester and/or plant stanol ester to the total amount of monosaccharides, disaccharides and sugar alcohols is preferably at least 1.7, more preferably at least 2.0, still more preferably at least 2.5, even more preferably at least 3.0 and most preferably at least 3.5.

Further in this embodiment, the weight ratio of the total fat to the oligosaccharide is preferably at least 1.4, more preferably at least 2.0, still more preferably at least 2.5, even more preferably at least 2.7 and most preferably at least 3.0. The weight ratio of the total fat to the oligosaccharide is preferably at most 8.0, more preferably at most 7.0 still more preferably at most 6.0, even more preferably at most 5.5 and most preferably at most 5.0.

In this embodiment, the amount of oligosaccharides in the composition is preferably at least 10%, more preferably at least 14%, still more preferably at least 18% and most preferably at least 20% by weight. In this embodiment, the amount of oligosaccharides in the composition is preferably at most 30%, more preferably at most 28%, and most preferably at most 25% by weight of the composition. The ratio of the total amount of oligosaccharides to the total amount of monosaccharides, disaccharides and sugar alcohols is then preferably from 1:0.2 to 1:0.8, and most preferably from 01:0.2 to 1:0.7. Moisture is then present in an amount of preferably at most 6% and most preferably at most 3% by weight.

Further in this embodiment, the amount of protein in the composition is preferably less than 10%, more preferably less than 5% by weight, and most preferably the composition is substantially protein free. The amount of starch is preferably less than 5%, more preferably less than 3% by weight, and most preferable the composition is substantially starch free. The amount of hydrocolloid in the composition is preferably less than 1.5%, more preferably less than 0.5% by weight, and most preferably the composition is substantially free of hydrocolloids.

Further in this embodiment the composition may contain one or more ingredients selected from the group consisting of flavorings, preparations from berries and/or fruits, cocoa powder, artificial sweeteners, colorants, preservatives, vitamins, antioxidants and probiotics.

The composition of this embodiment is preferably a chewable dietary supplement, more preferably a non-powdery chewable dietary supplement, still more preferably an uncooked non-powdery chewable dietary supplement, and most preferably an ungelled uncooked non-powdery chewable dietary supplement.

In this embodiment, preferably at least 2.5 g, more preferably at least 3.0 g and most preferably at least 3.4 g plant sterol ester and/or plant stanol ester is provided by 5-20 g, more preferably by 5-15 g, most preferably by 6-10 g of the composition.

Preferably at least 2.5 g, more preferably at least 3.0 g and most preferably at least 3.4 g plant sterol ester and/or plant stanol ester is provided by one serving of the dietary supplement of this embodiment, or by one serving of a biscuit or wafer containing the filling or topping of this embodiment.

Another preferred embodiment of the present invention is a serum LDL cholesterol lowering edible composition, which comprises
- total fat in an amount of 60-70% by weight, wherein the total fat comprises a mixture of a) plant sterol ester and/or plant stanol ester and b) triglyceride fat, the amount of plant sterol ester and/or plant stanol ester being at least 40% by weight of the composition and the amount of triglyceride fat being at least 20% by weight of the composition, provided that the amount of plant sterol ester and/or plant stanol ester is 50-70% by weight of the total fat,
- at least one monosaccharide, disaccharide or sugar alcohol in such an amount that the total amount of monosaccharides, disaccharides and sugar alcohols is 2-18% by weight,
- at least one oligosaccharide in such an amount that the ratio of the total amount of oligosaccharides to the total amount of monosaccharides, disaccharides and sugar alcohols is from 1:0.2 to 1:0.9, and
- moisture in an amount of at most 8% by weight.

In this embodiment the plant sterol ester and/or plant stanol ester comprises preferably plant stanol ester in an amount of at least 10%, more preferably at least 50%, still more preferably at least 70% and most preferably at least 90% by weight. The plant sterol ester and/or plant stanol ester has preferably a solid fat content (SFC) of at least 20%, more preferably at least 30%, still more preferably at least 40%, even more preferably at least 45% and most preferably at least 50% at 25° C.

In this embodiment, the amount of triglyceride fat is preferably at most 35%, more preferably at most 33% and most preferably at most 30% by weight of the composition. The triglyceride fat has preferably a solid fat content (SFC) of at least 30%, more preferably at least 35%, still more preferably at least 40%, even more preferably at least 45% and most preferably at least 50% at 25° C.

Further in this embodiment, the total fat in the composition preferably has a solid fat content (SFC) of at least 40%, more preferably at least 45%, and most preferably at least 50% at 25° C.

In this embodiment, the weight ratio of the plant sterol ester and/or plant stanol ester to the oligosaccharide is preferably at least 1.0, more preferably at least 1.3, still more preferably at least 1.5, even more preferably at least 1.7 and most preferably at least 2.0. The weight ratio of the plant sterol ester and/or plant stanol ester to the oligosaccharide is preferably at most 6.4, more preferably at most 6.0, still more preferably at most 5.0, even more preferably at most 4.0 and most preferably at most 3.5. The weight ratio of the plant sterol ester and/or plant stanol ester to the total amount of monosaccharides, disaccharides and sugar alcohols is preferably at least 1.7, more preferably at least 2.0, still more preferably at least 2.5, even more preferably at least 3.0 and most preferably at least 3.5.

Further in this embodiment, the weight ratio of the total fat to the oligosaccharide is preferably at least 1.4, more preferably at least 2.0, still more preferably at least 2.5, even more preferably at least 2.7 and most preferably at least 3.0. The weight ratio of the total fat to the oligosaccharide is preferably at most 8.0, more preferably at most 7.0 still more preferably at most 6.0, even more preferably at most 5.5 and most preferably at most 5.0.

In this embodiment, the amount of oligosaccharides in the composition is preferably at least 14%, still more preferably at least 18% and most preferably at least 20% by weight. In this embodiment, the amount of oligosaccharides in the composition is preferably at most 30%, more preferably at most 28%, and most preferably at most 25% by weight of the composition. The ratio of the total amount of oligosaccharides to the total amount of monosaccharides, disaccharides and sugar alcohols is then preferably from 1:0.2 to 1:0.8, and most preferably from 01:0.2 to 1:0.7.

Further in this embodiment, the amount of protein in the composition is preferably less than 10%, more preferably less than 5% by weight, and most preferably the composition is substantially protein free. The amount of starch is preferably less than 5%, more preferably less than 3% by weight, and most preferable the composition is substantially starch free. The amount of hydrocolloid in the composition is preferably less than 1.5%, more preferably less than 0.5% by weight, and most preferably the composition is substantially free of hydrocolloids.

Further in this embodiment the composition may contain one or more ingredients selected from the group consisting of flavorings, preparations from berries and/or fruits, cocoa powder, artificial sweeteners, colorants, preservatives, vitamins, antioxidants and probiotics.

The composition of this embodiment is preferably a chewable dietary supplement, more preferably a non-powdery chewable dietary supplement, still more preferably an uncooked non-powdery chewable dietary supplement, and most preferably an ungelled uncooked non-powdery chewable dietary supplement. Preferably at least 2.5 g, more preferably at least 3.0 g and most preferably at least 3.4 g plant sterol ester and/or plant stanol ester is provided by one serving of the dietary supplement of this embodiment, or by one serving of a biscuit or wafer containing the filling or topping of this embodiment.

Still another preferred embodiment of the present invention is a serum LDL cholesterol lowering edible composition, which comprises
- total fat in an amount of 55-80% by weight, wherein the total fat comprises a mixture of a) plant sterol ester and/or plant stanol ester and b) triglyceride fat, the amount of plant sterol ester and/or plant stanol ester being at least 37% by weight of the composition and the amount of triglyceride fat being at least 22% by weight of the composition, provided that the amount of plant sterol ester and/or plant stanol ester is 42-75% by weight of the total fat,
- at least one monosaccharide, disaccharide or sugar alcohol in such an amount that the total amount of monosaccharides, disaccharides and sugar alcohols is 3-16% by weight,
- at least one oligosaccharide in such an amount that the ratio of the total amount of oligosaccharides to the total amount of monosaccharides, disaccharides and sugar alcohols is from 1:0.2 to 1:0.9, and
- moisture in an amount of at most 8% by weight.

In this embodiment the plant sterol ester and/or plant stanol ester comprises preferably plant stanol ester in an amount of at least 10%, more preferably at least 50%, still more preferably at least 70% and most preferably at least 90% by weight. The plant sterol ester and/or plant stanol ester has preferably a solid fat content (SFC) of at least 20%, more preferably at least 30%, still more preferably at least 40%, even more preferably at least 45% and most preferably at least 50% at 25° C.

In this embodiment, the amount of triglyceride fat is preferably at most 35%, more preferably at most 33% and most preferably at most 30% by weight of the composition. The triglyceride fat has preferably a solid fat content (SFC) of at least 30%, more preferably at least 35%, still more preferably at least 40%, even more preferably at least 45% and most preferably at least 50% at 25° C.

Further in this embodiment, the total fat in the composition preferably has a solid fat content (SFC) of at least 40%, more preferably at least 45%, and most preferably at least 50% at 25° C.

In this embodiment, the weight ratio of the plant sterol ester and/or plant stanol ester to the oligosaccharide is preferably at least 1.0, more preferably at least 1.3, still more preferably at least 1.5, even more preferably at least 1.7 and most preferably at least 2.0. The weight ratio of the plant sterol ester and/or plant stanol ester to the oligosaccharide is preferably at most 6.4, more preferably at most 6.0, still more preferably at most 5.0, even more preferably at most 4.0 and most preferably at most 3.5. The weight ratio of the plant sterol ester and/or plant stanol ester to the total amount of monosaccharides, disaccharides and sugar alcohols is preferably at least 1.7, more preferably at least 2.0, still more preferably at least 2.5, even more preferably at least 3.0 and most preferably at least 3.5.

Further in this embodiment, the weight ratio of the total fat to the oligosaccharide is preferably at least 1.4, more preferably at least 2.0, still more preferably at least 2.5, even more preferably at least 2.7 and most preferably at least 3.0. The weight ratio of the total fat to the oligosaccharide is preferably at most 8.0, more preferably at most 7.0 still more preferably at most 6.0, even more preferably at most 5.5 and most preferably at most 5.0.

In this embodiment, the amount of oligosaccharides in the composition is preferably at least 10%, more preferably at least 14%, still more preferably at least 18% and most preferably at least 20% by weight. In this embodiment, the amount of oligosaccharides in the composition is preferably at most 30%, more preferably at most 28%, and most preferably at most 25% by weight of the composition. The ratio of the total amount of oligosaccharides to the total amount of monosaccharides, disaccharides and sugar alcohols is then preferably from 1:0.2 to 1:0.8, and most preferably from 01:0.2 to 1:0.7.

Further in this embodiment, the amount of protein in the composition is preferably less than 10%, more preferably less than 5% by weight, and most preferably the composition is substantially protein free. The amount of starch is preferably less than 3% by weight, and most preferable the composition is substantially starch free. The amount of hydrocolloid in the composition is preferably less than 1.5%, more preferably less than 0.5% by weight, and most preferably the composition is substantially free of hydrocolloids.

Further in this embodiment the composition may contain one or more ingredients selected from the group consisting of flavorings, preparations from berries and/or fruits, cocoa powder, artificial sweeteners, colorants, preservatives, vitamins, antioxidants and probiotics.

The composition of this embodiment is preferably a chewable dietary supplement, more preferably a non-powdery chewable dietary supplement, still more preferably an uncooked non-powdery chewable dietary supplement, and most preferably an ungelled uncooked non-powdery chewable dietary supplement.

In this embodiment, preferably at least 2.5 g, more preferably at least 3.0 g and most preferably at least 3.4 g plant sterol ester and/or plant stanol ester is provided by 5-15 g, most 2$ preferably by 6-10 g of the composition.

Preferably at least 2.5 g, more preferably at least 3.0 g and most preferably at least 3.4 g plant sterol ester and/or plant stanol ester is provided by one serving of the dietary supplement of this embodiment, or by one serving of a biscuit or wafer containing the filling or topping of this embodiment.

The invention further directed to a method for lowering serum LDL cholesterol in a subject in need thereof, wherein the composition according to the invention is administered to the subject i.e. the subject ingests the composition.

The plant sterol ester and/or plant stanol ester content of the composition of the present invention can be analyzed e.g. by a method described by Lubinus et al. (Eur. J. Nutr. 2013, 52(3):997-1013) or by Esche et al. (J. Agric. Food Chem. 2012, 30; 60(21):5330-9). The oligosaccharide content, as well as the monosaccharide, disaccharide and sugar alcohol content can be analysed e.g. by liquid chromatography. The triglyceride content can be analysed by separating triglycerides, e.g. with chromatography such as TLC, from the other lipid compounds obtained in the "total fat" extraction, and quantifying them e.g. with chromatographic methods.

The invention will be described in greater detail by means of the following non-limiting example. The percentages mean percentage by weight (wt %) unless otherwise stated.

Example 1 (Comparative)

Chewable dietary supplements were prepared with high plant sterol/stanol ester content (>30%) and high fat content (total fat >50%).

Plant stanol ester (Benecol Classic) was melted at 60° C. in its container. Cocoa butter substitute (Cargill) was melted at 50° C. in its container. 38 g of melted plant stanol ester and 22 g melted cocoa butter substitute were taken, and mixed together. Temperature of the fat mixture was kept at 50° C., and the fat mixture was mixed with 40 g of sucrose, corn starch, maltodextrin or gum. The composition was dosed into moulds and allowed to cool to room temperature (overnight). A trained sensory panel evaluated the supplements the following day.

Using disaccharide (sucrose), starch, oligosaccharide (a commercial maltodextrin containing 94.6% oligosaccharides, 1.3% monosaccharide and 4.1% disaccharide) or hydrocolloid (gum), together with the high content of total fat (60%) and plant stanol ester (38%), resulted in compositions that were unsatisfactory: soft, disintegrated and/or were adhesive to package material and hands, had unpleasant fatty/oily mouthfeel, were gritty, did not melt in mouth and left gum like or slimy pieces.

| % of the composition | Recipe 1 comparative | Recipe 2 comparative | Recipe 3 comparative | Recipe 4 comparative |
|---|---|---|---|---|
| Plant stanol ester (Benecol Classic) | 38 | 38 | 38 | 38 |
| Cocoa butter substitute (Cargill) | 22 | 22 | 22 | 22 |
| Sucrose | 40 | | | |
| Corn starch | | 40 | | |
| Maltodextrin (DE15) | | | 40 | |
| Gum (xanthan or guar) | | | | 40 |
| total | 100 | 100 | 100 | 100 |
| % total fat | 60 | 60 | 60 | 60 |
| % stanol ester of the total fat | 63 | 63 | 63 | 63 |
| Monosaccharides | 0 | 0 | 0.5 | 0 |
| Disaccharides | 40 | 0 | 1.6 | 0 |
| Sugar alcohols | 0 | 0 | 0 | 0 |
| Total amount of monosaccharides, disaccharides and sugar alcohols | 40 | 0 | 2.1 | 0 |
| Oligosaccharides | 0 | 0 | 37.8 | 0 |
| Ratio of the total amount of oligosaccharides to the total amount of monosaccharides, disaccharides and sugar alcohols | 0:1 | 0:0 | 1:0.06 | 0:0 |
| Mouthfeel | gritty, does not melt totally in mouth | melts in mouth, but leaves powdery and very oily/fatty mouthfeel, is like butter, unpleasant | gritty, does not melt totally in mouth, leaves "gum" like pieces | does not melt totally in mouth, leaves fatty film and slimy pieces in mouth |
| Other texture attributes | too soft, disintegrates, adhesive | too soft, disintegrates | adhesive | adhesive |

Example 2

In this example the effect of the amount of total monosaccharides, disaccharides and sugar alcohols in the composition, as well as the effects of the ratio of the total amount of oligosaccharides to the total amount of monosaccharides, disaccharides and sugar alcohols in relation to the quality and mouthfeel of the composition was tested. The compositions were prepared as in the example 1, only different amounts of ingredients were used. The dry ingredients (sucrose, xylitol and/or maltodextrin) were premixed together before mixing them with the fat mixture (plant stanol ester and cocoa butter substitute).

The amount of plant stanol ester (Benecol classic) 41% and cocoa butter substitute (Cargill) 24% by weight of the composition were used in all recipes 5-15. The total fat content of the compositions in recipes 5-15 was therefore 65% and the amount of plant stanol ester of the total fat was 63%.

A commercial maltodextrin was used as a source of oligosaccharides. The maltodextrin contained 94.6% oligosaccharides, 1.3% monosaccharide and 4.1% disaccharide.

| Recipe no | 5 | 6 | 7 | 8 | 9 | 10 | 11 | 12 | 13 | 14 | 15 |
|---|---|---|---|---|---|---|---|---|---|---|---|
| % of the composition | | | | | | | | | | | |
| Sucrose | | 2 | 5 | | 10 | 1 | 15 | 17 | 20 | 30 | 35 |
| Xylitol | | | | 5 | | 12 | | | | | |
| Maltodextrin (DE 15) | 35 | 33 | 30 | 30 | 25 | 22 | 20 | 18 | 15 | 5 | |
| Total amounts: | | | | | | | | | | | |
| Monosaccharides | 0.5 | 0.4 | 0.4 | 0.4 | 0.3 | 0.3 | 0.3 | 0.2 | 0.2 | 0.1 | 0 |
| Disaccharides | 1.4 | 3.4 | 6.2 | 1.2 | 11.0 | 1.9 | 15.8 | 17.7 | 20.6 | 30.2 | 35 |
| Sugar alcohols | 0 | 0 | 0 | 5 | 0 | 12 | 0 | 0 | 0 | 0 | 0 |
| Total amount of monosaccharides, disaccharides and sugar alcohols | 1.9 | 3.8 | 6.6 | 6.6 | 11.3 | 14.2 | 16.1 | 17.9 | 20.8 | 30.3 | 35 |

-continued

| Recipe no | 5 | 6 | 7 | 8 | 9 | 10 | 11 | 12 | 13 | 14 | 15 |
|---|---|---|---|---|---|---|---|---|---|---|---|
| Oligosaccharides | 33.1 | 31.2 | 28.4 | 28.4 | 23.7 | 20.8 | 18.9 | 17.0 | 14.2 | 4.7 | 0 |
| Ratio of the total amount of oligosaccharides to the total amount of monosaccharides, disaccharides and sugar alcohols | 1:0.06 | 1:0.1 | 1:0.2 | 1:0.2 | 1:0.5 | 1:0.7 | 1:0.9 | 1:1.1 | 1:1.5 | 1:6.4 | 0:1 |

Organoleptic Evaluation:

| | Mouthfeel | Other texture attributes | Overall rating |
|---|---|---|---|
| 5 | Leaves "gum like" pieces in the mouth, does not totally melt, gritty | Adhesive to package material and hands | – |
| 6 | Leaves only few "gum like" pieces in the mouth (less than recipe 5), does not totally melt, not gritty, no fatty/oily mouthfeel | Somewhat adhesive to package material and hands | + |
| 7 | Chewable, melts totally in mouth, does not leave "gum like" pieces or grittiness, no fatty/oily mouthfeel | Good, not adhesive | +++ |
| 8 | Chewable, melts totally in mouth, does not leave "gum like" pieces or grittiness, no fatty/oily mouthfeel | Good, not adhesive | +++ |
| 9 | Chewable, melts totally in mouth, does not leave "gum like" pieces or grittiness, no fatty/oily mouthfeel | Good, not adhesive | +++ |
| 10 | Chewable, melts totally in mouth, does not leave "gum like" pieces or grittiness, no fatty/oily mouthfeel | Good, not adhesive | +++ |
| 11 | Chewable, melts totally in mouth, does not leave "gum like" pieces or grittiness, no fatty/oily mouthfeel | Good, not adhesive, a bit softer than the recipes 7-10 | ++ |
| 12 | Does not melt totally in mouth, does not leave "gum like" pieces, but has some grittiness | Too soft, adhesive to package material and hands, disintegrates | – |
| 13 | More grittiness than in recipe 12, does not totally melt in mouth | Too soft, adhesive to package material and hands, melts partly in hands, disintegrates | – |
| 14 | More grittiness than in recipes 12 and 13, does not totally melt in mouth | Too soft, adhesive to package material and hands, melts partly in hands, disintegrates | – |
| 15 | Gritty, does not melt totally in mouth | Too soft, adhesive to package material and hands, disintegrates | – |

Despite the poor results that were achieved by using monosaccharide or disaccharide (recipes 1 and 15) or oligosaccharide (recipes 3 and 5) alone, it was surprisingly found that when using certain ratios of the total amount of oligosaccharides to the total amount of monosaccharides, disaccharides and sugar alcohols, compositions with the desired texture and mouthfeel characteristics were obtained. At the same time, the total amount of monosaccharides, disaccharides and/or sugar alcohols could be kept low.

Thus, a chewable composition with good texture and mouthfeel characteristics, and with a high plant sterol ester and/or plant stanol ester content, a high fat content and a low total content of monosaccharides, disaccharides and sugar alcohols could be prepared by a combination of oligosaccharide with monosaccharide, disaccharide and/or sugar alcohol in certain ratios.

Example 3

A Vanilla Flavoured Chewable Dietary Supplement was Prepared

| Ingredients | % of the composition |
|---|---|
| Plant stanol ester | 39 |
| Cocoa butter substitute | 24 |
| Sucrose | 8 |
| Sorbitol | 5 |
| Maltodextrin (DE 15) | 24 |
| *Vanilla* flavor | |
| Total | 100 |
| % total fat | 63 |
| % stanol ester of the total fat | 62 |
| % monosacharides | 0.3 |
| % disaccharides | 9.0 |
| % sugar alcohol | 5 |
| % oligosaccharides | 22.7 |

The ratio of total amount of oligosaccharides to the total amount of monosaccharides, disaccharides and sugar alcohols was 1:0.6. The serving size (9 g) contained 3.5 g plant stanol ester. The texture and the mouthfeel of the chewable dietary supplement was good.

Example 4

A Berry Flavored Chewable Dietary Supplement

| Ingredients | % of the composition |
| --- | --- |
| Plant sterol ester | 43 |
| Berry powder (blackcurrant) | 6 |
| Cocoa butter substitute | 25 |
| Fructose | 4 |
| Maltodextrin (DE 15) | 22 |
| Total | 100 |
| % total fat | 68 |
| % stanol ester of the total fat | 63 |
| % mono- and disaccharides | 8.8 |
| % oligosaccharides | 20.8 |

The berry powder contained 60% and the maltodextrin contained 5.4% sugars, so the total monosaccharide and disaccharide content of the composition was 8.8%. The ratio of total amount of oligosaccharides to the total amount of monosaccharides, disaccharides and sugar alcohols was 1:0.4. The serving size (8 g) contained 3.4 g plant sterol ester. The texture and the mouthfeel of the chewable dietary supplement was good.

Example 5

Cocoa Flavored Biscuit Filling

| Ingredients | % of the composition |
| --- | --- |
| Maltodextrin (DE 15) | 20 |
| Plant stanol ester | 42 |
| Instant cocoa powder | 5 |
| Cocoa butter substitute | 25 |
| Sucrose | 8 |
| Total | 100 |
| % total fat | 67 |
| % stanol ester of the total fat | 63 |
| % mono- and disaccharides | 10.1 |
| % oligosaccharides | 18.9 |

The cocoa powder contained 20% and the maltodextrin 5.4% sugar, so the total monosaccharide and disaccharide content of the composition was 10.1%. The ratio of total oligosaccharides to the total amount of monosaccharides, disaccharides and sugar alcohols was 1:0.5. The composition was used as a biscuit filling. One biscuit contained 6 g of the composition. Thus one serving (one biscuit) contained 2.5 g plant stanol ester. The texture and the mouthfeel of the filling was good.

Example 6

A Fruit Flavored Chewable Dietary Supplement

| Ingredients | % of the composition |
| --- | --- |
| Plant stanol ester | 38 |
| Dried apple (powder) | 8 |
| Cocoa butter substitute | 22 |
| Xylitol | 4 |
| Maltodextrin (DE 15) | 28 |
| Total | 100 |
| % total fat | 60 |
| % stanol ester of the total fat | 63 |
| % mono- and disaccharides | 10.3 |
| % oligosaccharides | 26.5 |

The apple powder contained 60% and the maltodextrin contained 5.4% sugars, so the total monosaccharide and disaccharide content of the composition was 10.3%. The ratio of total amount of oligosaccharides to the total amount of monosaccharides, disaccharides and sugar alcohols was 1:0.4. The serving size (8 g) contained 3.0 g plant stanol ester. The texture and the mouthfeel of the chewable dietary supplement was good.

Embodiments of the Invention

1. An edible composition comprising
total fat in an amount of at least 50% by weight, wherein the total fat comprises a mixture of a) plant sterol ester and/or plant stanol ester and b) triglyceride fat, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat,
at least one monosaccharide, disaccharide or sugar alcohol in such an amount that the total amount of monosaccharides, disaccharides and sugar alcohols is at most 18% by weight,
at least one oligosaccharide in such an amount that the ratio of the total amount of oligosaccharides to the total amount of monosaccharides, disaccharides and sugar alcohols is from 1:0.2 to 1:0.9, and
moisture in an amount of at most 8% by weight.

2. The composition according to embodiment 1, wherein it is a dietary supplement, a filling or a topping, preferably a dietary supplement, a biscuit filling or a wafer filling, more preferably a dietary supplement, and most preferably a chewable dietary supplement.

3. The composition according to embodiment 2, wherein at least 2.0 g, preferably at least 2.5 g, more preferably at least 3.0 g and most preferably at least 3.4 g plant sterol ester and/or plant stanol ester is provided by one serving of the dietary supplement, biscuit with filling or wafer with filling.

4. The composition according to any one of embodiments 1 to 3, wherein at least 2.0 g, preferably at least 2.5 g, more preferably at least 3.0 g and most preferably at least 3.4 g plant sterol ester and/or plant stanol ester is provided by 4-25 g, preferably 5-20 g, more preferably 5-15 g, most preferably 6-10 g of the composition.

5. The composition according to any one of embodiments 1 to 4, wherein the amount of total fat is 50-80%, preferably 55-80%, more preferably 60-75%, most preferably 60-70% by weight.

6. The composition according to any one of embodiments 1 to 5, wherein the total fat has a solid fat content (SFC) of at least 40%, preferably at least 45%, most preferably at least 50% at 25° C.

7. The composition according to any one of embodiments 1 to 6, wherein the amount of plant sterol ester and/or plant stanol ester is 40-80%, preferably 42-75%, more preferably 45-73%, most preferably 50-70% by weight of the total fat.

8. The composition according to any one of embodiments 1 to 6, wherein the amount of plant sterol ester and/or plant stanol ester is at least 34%, preferably at least 37%, more preferably at least 40%, most preferably at least 42% by weight of the composition.

9. The composition according to any one of embodiments 1 to 6 or 8, wherein the amount of plant sterol ester and/or plant stanol ester is at most 64%, preferably at most 60%, more preferably at most 58% and most preferably at most 56% of the composition.

10. The composition according to any one of embodiments 1 to 9, wherein the plant sterol ester and/or plant stanol ester has a solid fat content (SFC) of at least 20%, preferably at least 30%, more preferably at least 40%, still more preferably at least 45%, most preferably at least 50% at 25° C.

11. The composition according to any one of embodiments 1 to 10, wherein the plant sterol ester and/or plant stanol ester comprises plant stanol ester in an amount of at least 10%, preferably at least 50%, more preferably at least 70%, and most preferably at least 90% by weight.

12. The composition according to any one of embodiments 1 to 11, wherein the amount of triglyceride fat is at least 15%, preferably at least 17%, more preferably more than 20%, still more preferably at least 22%, even more preferably at least 24% and most preferably at least 25% by weight.

13. The composition according to any one of embodiments 1 to 12, wherein the amount of triglyceride fat is at most 35%, preferably at most 33% and most preferably at most 30% by weight of the composition.

14. The composition according to any one of embodiments 1 to 13, wherein the triglyceride fat has a solid fat content (SFC) of at least 30%, preferably at least 35%, more preferably at least 40%, still more preferably at least 45%, most preferably at least 50% at 25° C.

15. The composition according to any one of embodiments 1 to 14, wherein the triglyceride fat comprises cocoa butter, cocoa butter substitute, cocoa butter replacer and/or cocoa butter equivalent and/or wherein the triglyceride fat is cocoa butter, cocoa butter substitute, cocoa butter replacer and/or cocoa butter equivalent.

16. The composition according to any one of embodiments 1 to 5, wherein the total amount of monosaccharides, disaccharides and sugar alcohols is 2-18%, preferably 3-16% and most preferably 5-15% by weight of the composition.

17. The composition according to any one of embodiments 1 to 16, wherein the amount of oligosaccharides is at least 10%, preferably at least 14%, more preferably at least 18%, most preferably at least 20% by weight of the composition.

18. The composition according to any one of embodiments 1 to 17, wherein the amount of oligosaccharides is at most 30%, preferably at most 28%, most preferably at most 25% by weight of the composition.

19. The composition according to any one of embodiments 1 to 18, wherein the ratio of the total amount of oligosaccharides to the total amount of monosaccharides, disaccharides and sugar alcohols is from 1:0.2 to 1:0.9, preferably from 1:0.2 to 1:0.8, and most preferably from 1:0.2 to 1:0.7.

20. The composition according to any one of embodiments 1 to 19, wherein the oligosaccharides comprise maltodextrin.

21. The composition according to any one of embodiments 1 to 20, wherein the weight ratio of the plant sterol ester and/or plant stanol ester to the oligosaccharide is at least 1.0, preferably at least 1.3, more preferably at least 1.5, still more preferably at least 1.7 and most preferably at least 2.0.

22. The composition according to any one of embodiments 1 to 21, wherein the weight ratio of the plant sterol ester and/or plant stanol ester to the oligosaccharide is at most 6.4, preferably at most 6.0, more preferably at most 5.0, still more preferably at most 4.0 and most preferably at most 3.5.

23. The composition according to any one of embodiments 1 to 22, wherein the weight ratio of the total fat to the oligosaccharide is at least 1.4, preferably at least 2.0, more preferably at least 2.5, still more preferably at least 2.7 and most preferably at least 3.0.

24. The composition according to any one of embodiments 1 to 23, wherein the weight ratio of the total fat to the oligosaccharide is at most 8.0, preferably at most 7.0 more preferably at most 6.0, still more preferably at most 5.5 and most preferably at most 5.0.

25. The composition according to any one of embodiments 1 to 24, wherein the weight ratio of the plant sterol ester and/or plant stanol ester to the total amount of monosaccharides, disaccharides and sugar alcohols is at least 1.7, preferably at least 2.0, more preferably at least 2.5, still more preferably at least 3.0 and most preferably at least 3.5.

26. The composition according to any one of embodiments 1 to 25, wherein it further comprises one or more other ingredients selected from the group consisting of flavorings;

preparations from fruits and berries, such as berry powders and fruit powders; cocoa powder; artificial sweeteners; colorants; preservatives; and ingredients with beneficial health effects, such as vitamins, antioxidants, polyphenols and/or probiotics.

27. The composition according to any one of embodiments 1 to 26, wherein the protein content is less than 10%, more preferably less than 5%, still more preferably less than 3% and even further preferably less than 1% by weight of the composition, and most preferably the composition contains no protein.

28. The composition according to any one of embodiments 1 to 27, wherein the starch content is less than 5%, preferably less than 4%, more preferably less than 3%, and still more preferably less than 2% by weight of the composition, and most preferably the composition contains no starch.

29. The composition according to any one of embodiments 1 to 28, wherein the hydrocolloid content is less than 2%, preferably less than 1.5%, more preferably less than 1%, still more preferably less than 0.5% by weight of the composition, and most preferably the composition contains no hydrocolloid.

30. The composition according to any one of embodiments 1 to 29, wherein it is emulsifier-free.

31. The composition according to any one of embodiments 1 to 30, wherein no water has been added during the preparation process of the composition.

32. The composition according to any one of embodiments 1 to 31, wherein the composition has at least one of the features selected from the group chewable, non-powdery, melts in the mouth, ungelled and uncooked.

33. A method for preparing the edible composition according to any one of embodiments 1 to 32, wherein the method comprises following steps:
melting the plant sterol ester and/or plant stanol ester, preferably at a temperature of at least 40° C., more preferably at 40-80° C.,
mixing the melted plant sterol ester and/or plant stanol ester with the triglyceride fat, which has preferably been melted, preferably at a temperature of at least 40° C., more preferably at 40-80° C.,
mixing the obtained fat mixture, which has a temperature of at least 40° C., more preferably 40-80° C. to avoid its crystallization, with the other ingredients,
optionally forming the desired shapes, and
optionally packaging the composition,
the method preferably excluding any step of adding water and/or cooking the mixture of ingredients to substantially reduce the moisture content of the mixture of ingredients during the preparation of the composition.

34. The method according to embodiment 33 for preparing a dietary supplement, wherein the method comprises following steps:
melting the plant sterol ester and/or plant stanol ester, preferably at a temperature of at least 40° C., more preferably at 40-80° C.,
mixing the melted plant sterol ester and/or plant stanol ester with the triglyceride fat, which has preferably been melted, preferably at a temperature of at least 40° C., more preferably at 40-80° C.,
mixing the obtained fat mixture, which has a temperature of at least 40° C., more preferably 40-80° C. to avoid its crystallization, with the other ingredients,
forming the desired shapes, and
packaging the composition,
the method preferably excluding any step of adding water and/or cooking the mixture of ingredients to substantially reduce the moisture content of the mixture of ingredients during the preparation of the composition.

35. Use of an edible composition according to any one of embodiments 1 to 32 for preparation of a dietary supplement, a biscuit with filling or topping or a wafer with filling or topping.

36. The edible composition according to any one of embodiments 1 to 32 for use as a medicament and/or for lowering serum LDL cholesterol level.

37. A method for lowering serum LDL cholesterol in a subject in need thereof, wherein the subject ingests the edible composition according to any one of embodiments 1 to 32.

The invention claimed is:

1. An edible composition for lowering LDL serum cholesterol in a human in need thereof consisting essentially of:
total fat in an amount of at least 50% by weight, wherein the total fat consists essentially of a mixture of: a) plant sterol ester and/or plant stanol ester; and b) triglyceride fat, selected from the group consisting of cocoa butter or cocoa butter substitute, the amount of plant sterol ester and/or plant stanol ester being at least 30% by weight of the composition and the amount of triglyceride fat being at least 10% by weight of the composition, provided that the amount of plant sterol ester and/or plant stanol ester is at least 40% by weight of the total fat;
at least one of: (i) a monosaccharide selected from the group consisting of glucose, fructose, galactose and xylose, (ii) a disaccharide selected from the group consisting of sucrose, lactose and maltose or (iii) a sugar alcohol selected from the group consisting of sorbitol, erythritol, xylitol, mannitol, lactitol, isomalt and maltitol, wherein the total amount of monosaccharides, disaccharides and/or sugar alcohols is at most 18% by weight; and
maltodextrin;
wherein the ratio of the maltodextrin to the total amount of monosaccharides, disaccharides and/or sugar alcohols is from 1:0.2 to 1:0.9 and the total amount of moisture in the edible composition is in an amount of at most 8% by weight.

2. The edible composition of claim 1, which is a dietary supplement, a filling or a topping.

3. The edible composition of claim 1, wherein one serving of the dietary supplement, filling or topping contains at least 2.0 g plant sterol ester and/or plant stanol ester.

4. The edible composition of claim 1, wherein the amount of total fat is 50-80% by weight of the edible composition.

5. The edible composition of claim 1, wherein the amount of plant sterol ester and/or plant stanol ester is 40-80% by weight of the total fat of the edible composition.

6. The edible composition of claim 1, wherein the amount of plant sterol ester and/or plant stanol ester is at least 34% by weight of the edible composition.

7. The edible composition of claim 1, wherein the total amount of monosaccharides, disaccharides and sugar alcohols is 2-18% by weight of the edible composition.

8. The edible composition of claim 1, wherein the amount of maltodextrin is at least 10% by weight of the edible composition.

9. The edible composition of claim 1, further consisting essentially of berry powders, fruit powders; cocoa powder; artificial sweeteners; preservatives; vitamins; antioxidants; polyphenols and/or probiotics.

10. The edible composition of claim 1, wherein the protein content is less than 10% by weight of the edible composition.

11. The edible composition of claim 1, wherein it is emulsifier-free and/or wherein no water is added during the preparation process of the edible composition and/or wherein the edible composition has at least one of the features selected from the group consisting of chewable, non-powdery, melts in the mouth, ungelled and uncooked.

12. The edible composition of claim 1, wherein the plant sterol ester and/or plant stanol ester consist essentially of plant stanol ester in an amount of at least 10% by weight of the edible composition.

13. A method for preparing the edible composition of claim 1, consisting essentially of the following steps:
melting the plant sterol ester and/or plant stanol ester at a temperature of between about 40° C.-80° C.,
mixing the melted plant sterol ester and/or plant stanol ester with the triglyceride fat, which has been melted, at a temperature of between about 40° C.-80° C.,
mixing the obtained fat mixture, which has a temperature of at least 40° C. to avoid its crystallization, with the at least one monosaccharide, disaccharide and/or sugar alcohol and the maltodextrin to form the edible composition of claim 1.

14. The method of claim 13, wherein the edible composition is a dietary supplement, a filling for a biscuit or a wafer, or a topping for a biscuit or a wafer.

15. The composition of claim 1, wherein the starch content is less than 5% by weight of the edible composition.

16. The composition of claim 1, wherein the edible composition has a hydrocolloid content less than 2% by weight of the edible composition.

17. The method of claim 13, which further consists essentially of shaping the edible composition and then packaging it.

18. The method of claim 13, wherein the method excludes at least one of a step of adding water or cooking the edible composition to substantially reduce the moisture content of the edible composition during the preparation method.

* * * * *